US 9,810,604 B2

(12) United States Patent
Yotani et al.

(10) Patent No.: US 9,810,604 B2
(45) Date of Patent: Nov. 7, 2017

(54) SAMPLE INJECTION DEVICE FOR FLOW-TYPE ANALYSIS DEVICE, FLOW-TYPE ANALYSIS DEVICE, AND MEASUREMENT METHOD FOR HEMOGLOBIN COMPONENT

(71) Applicant: Sekisui Medical Co., Ltd., Tokyo (JP)

(72) Inventors: Takuya Yotani, Tokyo (JP); Takayuki Oka, Tokyo (JP); Hideki Muraki, Tokyo (JP)

(73) Assignee: Sekisui Medical Co., Ltd. (JP)

( * ) Notice: Subject to any disclaimer, the term of this patent is extended or adjusted under 35 U.S.C. 154(b) by 50 days.

(21) Appl. No.: 14/781,200

(22) PCT Filed: Mar. 27, 2014

(86) PCT No.: PCT/JP2014/058829
§ 371 (c)(1),
(2) Date: Sep. 29, 2015

(87) PCT Pub. No.: WO2014/157505
PCT Pub. Date: Oct. 2, 2014

(65) Prior Publication Data
US 2016/0041072 A1 Feb. 11, 2016

(30) Foreign Application Priority Data
Mar. 29, 2013 (JP) .................. 2013-073455

(51) Int. Cl.
*G01N 35/10* (2006.01)
*G01N 1/14* (2006.01)
(Continued)

(52) U.S. Cl.
CPC ........... *G01N 1/14* (2013.01); *G01N 15/1429* (2013.01); *G01N 30/16* (2013.01); *G01N 30/18* (2013.01);
(Continued)

(58) Field of Classification Search
None
See application file for complete search history.

(56) References Cited

U.S. PATENT DOCUMENTS 4,094,195 A 6/1978 Friswell et al.
4,094,196 A * 6/1978 Friswell ................. G01N 30/24
73/864.21
(Continued)

FOREIGN PATENT DOCUMENTS

CN 101765775 A 6/2010
JP S57-66358 A 4/1982
(Continued)

OTHER PUBLICATIONS

Extended European Search Report dated Oct. 10, 2016, for European Patent Application No. 14776033, 9 pages.
(Continued)

*Primary Examiner* — Robert R Raevis
(74) *Attorney, Agent, or Firm* — Lerner, David, Littenberg, Krumholz & Mentlik, LLP

(57) ABSTRACT

Provided is a sample injection device for flow-type analysis including a cylindrical needle (27) which penetrates through an upper wall and a lower wall of a sample injection portion (22) of a carrier-liquid channel through ring-like sealing members (25, 26). The needle (27) includes an inner hole (41) which is closed on a side of a lower end of the needle (27) and open on an outer peripheral surface as a horizontal hole (42). The needle moving unit (44) induces the needle (27) to move downward so that the horizontal hole (42) faces an inside of a sample vessel (40) to draw the sample to the inside of the needle (27). Then the moving unit (44) induces the needle (27) to move upward so that the horizontal hole (42) faces an inside of the sample injection portion (22) to inject the sample in the inside of the needle (27). At an intermediate position, washing liquid is discharged from the
(Continued)

horizontal hole (42) of the needle (27), and the washing liquid is recovered via a discharge path (15).

10 Claims, 5 Drawing Sheets

(51) Int. Cl.
    *G01N 30/16*     (2006.01)
    *G01N 15/14*     (2006.01)
    *G01N 33/49*     (2006.01)
    *G01N 30/18*     (2006.01)
    *G01N 30/88*     (2006.01)

(52) U.S. Cl.
    CPC ....... *G01N 33/491* (2013.01); *G01N 33/4915* (2013.01); *G01N 35/1095* (2013.01); *G01N 35/1016* (2013.01); *G01N 2015/1486* (2013.01); *G01N 2030/8822* (2013.01)

(56) References Cited

U.S. PATENT DOCUMENTS

| | | |
|---|---|---|
| 5,820,824 A | 10/1998 | Tanaka |
| 2011/0189713 A1* | 8/2011 | Le Comte ................ G01N 1/38 435/29 |

FOREIGN PATENT DOCUMENTS

| | | |
|---|---|---|
| JP | S63-84562 U | 6/1988 |
| JP | H05-256834 A | 10/1993 |
| JP | H07-311127 A | 11/1995 |
| JP | H09-171023 A | 6/1997 |
| JP | H09-304368 A | 11/1997 |
| JP | 2011-013045 A | 1/2011 |

OTHER PUBLICATIONS

International Search Report from International Publication PCT/JP2014/058829 dated Jul. 1, 2014.

* cited by examiner

SAMPLE INJECTION DEVICE FOR FLOW-TYPE ANALYSIS DEVICE, FLOW-TYPE ANALYSIS DEVICE, AND MEASUREMENT METHOD FOR HEMOGLOBIN COMPONENT

CROSS-REFERENCE TO RELATED APPLICATIONS

The present application is a national phase entry under 35 U.S.C. §371 of International Application No. PCT/JP2014/058829 filed Mar. 27, 2014, published in Japanese, which claims priority from Japanese Patent Application No. 2013-073455 filed on Mar. 29, 2013, the disclosures of which are hereby incorporated by reference in their entirety.

TECNICAL FIELD

The present invention relates to a sample injection device for a flow-type analysis device for superior injection of a sample into a carrier-liquid channel, and further relates to a flow-type analysis device that uses the sample injection device, and to a measurement method for hemoglobin components, such as hemoglobin A1c.

BACKGROUND ART

As a conventional sample injection device for a flow-type analysis device of this type, the device disclosed in Patent Document 1 is known. In this device, a sample injection valve is provided in a carrier-liquid (eluant) channel which allows the carrier liquid to flow into a column by means of a pump, and the valve has a sample drawing position and a sample injection position.

In addition, it is necessary to wash the needle each time a new sample is drawn, and a needle washing unit for the washing is separately provided.

At the sample drawing position, the upper flow channel and the lower flow channel of the carrier-liquid channel are connected as a short circuit, and on the other hand, the sample loop is separated from the carrier-liquid channel, and the sample is drawn into the sample loop in this state.

At the sample injection position, the upper flow channel and the lower flow channel of the carrier-liquid channel are connected via the sample loop, and thereby, the sample is injected into the flow of the carrier liquid.

In addition, after the sample is injected, the needle is moved to a needle washing position, which is separately provided, to undergo washing.

REFERENCE DOCUMENT LIST

Patent Document

Patent Document 1: Japanese Patent Application Laid-Open Publication No. H05-256834

SUMMARY OF THE INVENTION

Problems to be Solved by the Invention

However, in the conventional sample injection device, in shifting from the sample drawing position to the sample injection position, the carrier-liquid channel is temporarily blocked, and therefore, the flow of the carrier liquid is disturbed. In addition, when the sample loop is connected to the carrier-liquid channel, the flow rate is changed due to pressure fluctuation because the pressure in the carrier-liquid channel is high while the inside of the sample loop is at atmospheric pressure, and this change of the flow rate also causes disturbance in the flow. Thus, a phenomenon known as "injection shock" may occur, which adversely affects the analysis.

Note that in the device disclosed in Patent Document 1, shifting between constant flow rate control and constant pressure control is carried out to prevent injection shock; however, it is difficult to carry out the control with high precision due to response lags in the control and the like, and this is considered to at least interrupt an increase in the speed of analyses.

In a conventional sample injection device, a washing position is separately provided for washing of the needle carried out after a sample is injected, and because a large area for installing a washing unit and a large amount of washing liquid are necessary to increase the washing efficiency, it becomes difficult to reduce the size of the device and to maintain the washing efficiency.

In consideration of the above situation, the purpose of the invention is to provide a sample injection device for a flow-type analysis device capable of superior injection of a sample into a flow of a carrier liquid, without producing injection shocks.

Means for Solving the Problems

In order to solve the above-described problem, according to an aspect of the present invention, a sample injection device according to the present invention includes a cylindrical needle which extends in a vertical direction and penetrates through an upper wall and a lower wall of the carrier-liquid channel at a sample injection position; ring-like sealing members that seal the penetrated portions; a vessel holding portion arranged below the lower wall and which holds a vessel in which a sample is contained; a needle moving unit capable of causing the needle to move in a vertical direction; and a measurement pump which can be connected with the needle on an upper end of the needle.

The cylindrical needle includes an inner hole that is closed on a side of the lower end thereof and open on an outer peripheral surface as a horizontal hole.

The needle moving unit is capable of causing the needle to move to at least a sample drawing position at which the horizontal hole is positioned below the lower wall and faces an inside of the vessel and a sample injection position at which the horizontal hole is positioned above the lower wall and faces the carrier-liquid channel.

The measurement pump is connected to the cylindrical needle on the upper end of the needle and configured to perform a drawing operation when the needle is positioned at the sample drawing position and a discharge operation when the needle is positioned at the sample injection position.

In addition, according to an aspect of the present invention, it is preferable that a washing position be set at a position between the sample drawing position and the sample injection position outside the carrier-liquid channel as a position for the needle to move by being induced by the needle moving unit, and that the sample injection device further include a washing liquid feed device capable of feeding washing liquid to an inside of the needle to discharge the washing liquid through the horizontal hole when the needle is positioned at the washing position; and a washing liquid recovery device configured to recover the washing liquid that flows out through the horizontal hole when the needle is positioned at the washing position by surrounding the needle.

According to another aspect of the present invention, a flow-type analysis device includes the above-described sample injection device; and a detection device which is arranged in the carrier-liquid channel on a downstream side of the sample injection device and configured to detect components of the sample. It is preferable that the flow-type analysis device further include a separation device which is provided in the carrier-liquid channel between the sample injection device and the detection device and be configured to separate components of the sample.

In addition, the above-described flow-type analysis device can be preferably used for measuring hemoglobin components (in particular, hemoglobin A1c) in diabetes testing. Accordingly, in a measurement method for hemoglobin components according to an aspect of the present invention, blood is injected into the carrier-liquid channel as the sample using the above-described sample injection device; and hemoglobin components contained in the blood are separated and detected and the amount of the components (hemoglobin A1c and the like) is measured.

Note that in this specification, the term "blood" used for measurement of hemoglobin components refers to a sample containing red blood cells, such as whole blood, whole blood diluted with a buffer solution or the like, a red blood cell fraction obtained by natural precipitation or centrifugal separation, washed red blood cells, a blood-dissolved solution treated by hemolysis, and the like.

Examples of the flow-type analysis device include a flow cytometer, a flow injection analysis device, liquid chromatography, and the like.

Effects of the Invention

According to the sample injection device of the present invention, the needle, which penetrates through the upper wall and the lower wall in the carrier-liquid channel, is caused to move so that the horizontal hole included in the needle is positioned at the sample drawing position outside the carrier-liquid channel, then the sample is drawn, then the needle is moved so that the horizontal hole thereof is positioned to the sample injection position in the carrier-liquid channel, and thereby the sample can be injected.

With this configuration, the carrier-liquid channel is not blocked when the sample is injected and the carrier-liquid channel is always in substantially the same state, which enables elimination of the occurrence of sample injection shocks, and thus, constant flow superior injection of samples into a constant flow of carrier-liquid can be realized.

In addition, according to the present invention, conventional sample injection valves and the like become unnecessary, and thus reduction in size and price of the device can be achieved. Furthermore, maintenance of the device can be readily performed.

In particular, by employing the horizontal hole structure for the needle instead of an open tip structure, it becomes unnecessary to cause the needle to go from the lower wall toward the sample injection portion when injecting a sample, and thus, the needle can always remain penetrated through the lower wall. Accordingly, the general ring-like sealing members can be applied to the penetrated portions. With this configuration, the durability and the reliability can be improved.

Furthermore, with the needle washing mechanism formed integrally with the mechanism of the sample injection device, the mechanism may not require an additional area for installation of a separately provided washing unit.

Accordingly, by configuring the flow-type analysis device by using the sample injection device having the above-described configuration, not only can an analysis with a high precision and a high performance be achieved, but also downsizing and the like of the device can be achieved.

In addition, by measuring hemoglobin components (in particular, hemoglobin A1c) contained in blood by liquid chromatography by using the sample injection device described above, it is possible to carry out the measurement with high precision and at high speed.

MODE FOR CARRING OUT THE INVENTION

Figure 1:
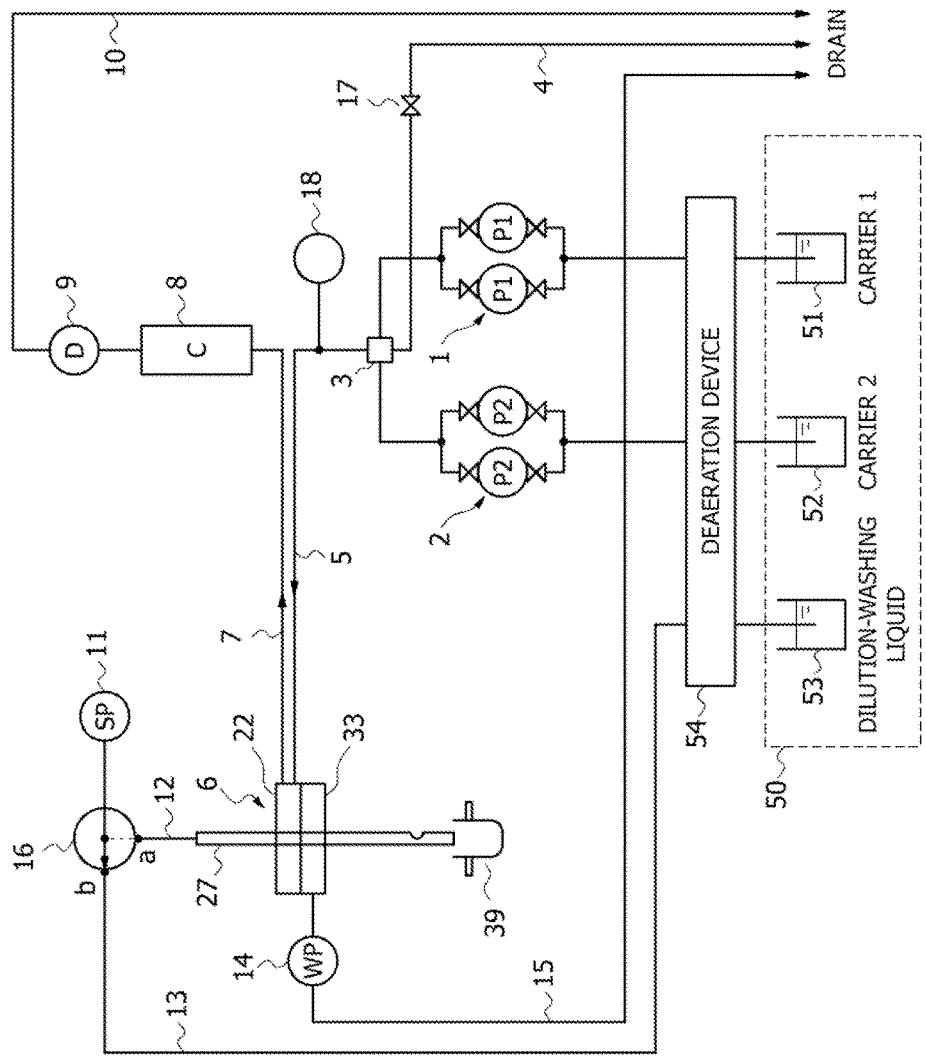
FIG. 1 is a system view illustrating an embodiment of a flow-type analysis device including a sample injection device according to the present invention.

An embodiment of the invention will be described below. FIG. 1 is a system view illustrating an embodiment of a flow-type analysis device including a sample injection device according to the present invention.

The flow-type analysis device according to the present embodiment is used to analyze respective hemoglobin components included in blood, such as hemoglobin A1c, using high-performance liquid chromatography (HPLC). Accordingly, the sample is blood. In addition, hemolysis treatment is necessary as a pretreatment and hemolysis liquid is used, and a dilution liquid for which hemolysis can be performed at the same time as dilution, and further, hemolysis-dilution-washing liquid, which is used for multiple purposes of hemolysis, dilution, and washing, is used as the hemolysis liquid.

A flow-type analysis device illustrated in FIG. 1 includes carrier-liquid tanks 51, 52 for first carrier liquid and second carrier liquid with different solution compositions, and a dilution-washing liquid tank 53, which are connected to the analysis device via a common deaeration device 54. Note that the first and the second carrier-liquid tanks 51, 52 and the dilution-washing liquid tank 53 may be formed as a reagent kit 50. Further, the dilution-washing liquid tank 53 may be divided into mutually separate individual tanks, i.e., into a dilution liquid tank 53a and a washing-liquid tank 53b.

The flow-type analysis device illustrated in FIG. 1 includes liquid feed pumps 1, 2 for feeding the first and the second carrier liquid from the first and the second carrier-liquid tanks 51, 52; a 4-way joint 3 for mixing the carrier liquid fed from the liquid feed pumps 1, 2; a discharge path 4 for discharging waste liquid from the 4-way joint 3; a carrier-liquid channel 5 for feeding the carrier liquid from the 4-way joint 3, a drain valve 17 provided in the discharge path 4; a pressure sensor 18 provided in the channel 5; a sample injection device (main body) 6 to which the channel 5 is connected to an inlet port thereof; a carrier-liquid channel 7 connected to the sample injection device 6 at an outlet port thereof; a column 8 and a detection unit 9 provided in the channel 7; and a discharge path 10 provided on a downstream side of the column 8 and the detection unit 9.

The liquid feed pumps 1, 2 for feeding the first and the second carrier liquid are a double plunger pump, respectively, and respectively include check valves (one-way valves) provided at a drawing port and a discharge port. In addition, the liquid feed pumps 1,2 are a variable capacity type pump of which a discharge capacity can be changed by changing a stroke of the plunger, respectively, and thus, the flow rate between the two liquid feed pumps 1, 2 can be changed.

The 4-way joint 3 mixes the first carrier liquid from the liquid feed pump 1 and the second carrier liquid from the liquid feed pump 2 together. Accordingly, by changing the flow rate between the liquid feed pumps 1, 2 and by mixing the carrier liquid by using the 4-way joint 3, a carrier liquid with an arbitrary concentration in between the concentration of the first carrier liquid and the concentration of the second carrier liquid (a gradient function).

The sample injection device (main body) 6, of which the structure will be described in detail below, includes a sample injection portion 22. The sample injection portion 22 is provided between the channel 5 for the carrier liquid from the 4-way joint 3 and the flow path 7 provided on a downstream side thereof, and is capable of injecting a sample into the carrier liquid with the needle 27 having been moved to a sample injection position.

The sample injection device 6 also includes a sample drawing portion (vessel holding portion) 39 provided below the sample injection portion 22. The sample drawing portion 39 can draw in the sample with the needle 27 having been moved to a sample drawing position. Accordingly, the sample drawn by the sample drawing portion 39 is injected by the sample injection portion 22 into the carrier liquid. Note that the drawing and the injection are carried out by connecting a measurement pump 11 to a pipe 12 of the needle 27 via a switching valve 16.

The sample injection device 6 also includes a washing portion 33 for washing the needle 27, which is provided integrally with a housing 21 of the sample injection portion 22 between the sample injection portion 22 and the sample drawing portion 39. The washing portion 33 supplies washing liquid and washes the needle 27 having been moved to a washing position. The washing is carried out by connecting the measurement pump 11 to a pipe 13 from the dilution-washing liquid tank 53 via the switching valve 16, then drawing the washing liquid, and then connecting the measurement pump 11 to the pipe 12 of the needle 27 via the switching valve 16. After the washing is completed, the washing liquid is recovered by a discharge pump 14 and the recovered washing liquid is discharged into a discharge path 15.

The column 8 is provided in the carrier-liquid channel 7 of on a downstream side of the sample injection device 6 and separates components of the sample.

The detection unit 9 is provided on a downstream side of the column 8, detects the separated components, and transmits a detection signal thereof to a data processing apparatus (not illustrated). Results of the data processing by the data processing apparatus are output as analysis results.

The flow-type analysis device illustrated in FIG. 1 includes the switching valve 16 for switching the channel, and the switching valve 16 can be positioned at two positions a, b. The two positions a, b correspond to ports a, b, respectively, to which an in-valve channel 16a that communicates with the measurement pump 11 is selectively connected as the in-valve channel 16a turns.

The port a is connected to the needle 27 of the sample injection device 6 via the pipe 12.

The port b is connected to the dilution-washing liquid tank 53 via the pipe 13.

Deaeration and charging of the carrier liquid performed at the stage of operation preparation of the flow-type analysis device illustrated in FIG. 1 will be described below.

The following operation performed at the stage of the operation preparation has been well known to persons skilled in the art, which is performed to deaerate the inside of the channels and charge the inside of the channels with liquid.

The drain valve 17 is opened, and the liquid feed pumps 1, 2 are driven for a few minutes at the flow rate determined in accordance with the volume of a liquid contact part of the check valve of the liquid feed pumps 1, 2 to deaerate the inside of the channels (e.g., at the flow rate of 2 mL/min for 5 minutes, and the like).

A dilution step, a sample drawing step, a sample injection step, and a washing step, which are performed during a normal operation of the flow-type analysis device illustrated in FIG. 1, will be described.

In the dilution step, the needle 27 of the sample injection device 6 is positioned at the sample drawing position (the sample drawing portion 39), i.e., at a position inside a vessel that accommodates the sample.

The switching valve 16 is first positioned at the position b. At the position b, the measurement pump 11 is connected to the port b (the pipe 13). In this state, the drawing operation of the measurement pump 11 is performed. Then, the dilution liquid (dilution-washing liquid) in the dilution-washing liquid tank 53 is drawn into the measurement pump 11 through the pipe 13.

The switching valve 16 is then positioned to the position a. At the position a, the measurement pump 11 is connected to the port a (the pipe 12). In this state, the discharge operation of the measurement pump 11 is performed. Then, the washing liquid in the measurement pump 11 is pumped to the inside of the needle 27 through the pipe 12. The needle 27 is positioned at the sample drawing position (the sample drawing portion 39), i.e., in the inside of the vessel, and thus the dilution liquid is supplied into the vessel.

In the sample drawing step, the needle 27 of the sample injection device 6 is positioned at the sample drawing position (the sample drawing portion 39), i.e., in the inside of the vessel that accommodates the sample (the sample diluted with the dilution liquid).

The switching valve 16 is positioned to the position a. At the position a, the measurement pump 11 is connected to the port a (the pipe 12). In this state, the drawing operation of the measurement pump 11 is performed. Then, the sample in the vessel is drawn to the inside of the needle 27.

In the sample injection step, the needle 27 of the sample injection device 6 is positioned to the sample injection position (the sample injection portion 22).

The switching valve 16 is disposed at position a. At the position a, the measurement pump 11 is connected to the port a (the pipe 12). In this state, the discharge operation of the measurement pump 11 is performed. Then, the sample in the needle 27 is injected into the sample injection portion 22 arranged between the carrier-liquid channels 5, 7.

In the washing step, the needle 27 of the sample injection device 6 is disposed at the washing position (the washing portion 33) between the sample drawing position and the sample injection position.

The switching valve 16 is first disposed at position b. At the position b, the measurement pump 11 is connected to the port b (the pipe 13). In this state, the drawing operation of the measurement pump 11 is performed. Then, the washing liquid (the dilution-washing liquid) in the dilution-washing liquid tank 53 is drawn into the measurement pump 11 through the pipe 13.

The switching valve 16 is then disposed at the position a. At the position a, the measurement pump 11 is connected to the port a (the pipe 12). In this state, the discharge operation of the measurement pump 11 is performed. Then, the washing liquid in the measurement pump 11 is pumped to the inside of the needle 27 through the pipe 12. The needle 27 is positioned at the washing position (the washing portion 33), and the needle 27 is washed with the washing liquid. After the washing is completed, the washing liquid is recovered by the discharge pump 14, and the recovered washing liquid is then discharged through the discharge path 15.

Next, the detailed structure of the sample injection device (main body) 6 will be described with reference to FIGS. 2 to 4.

Figure 2:
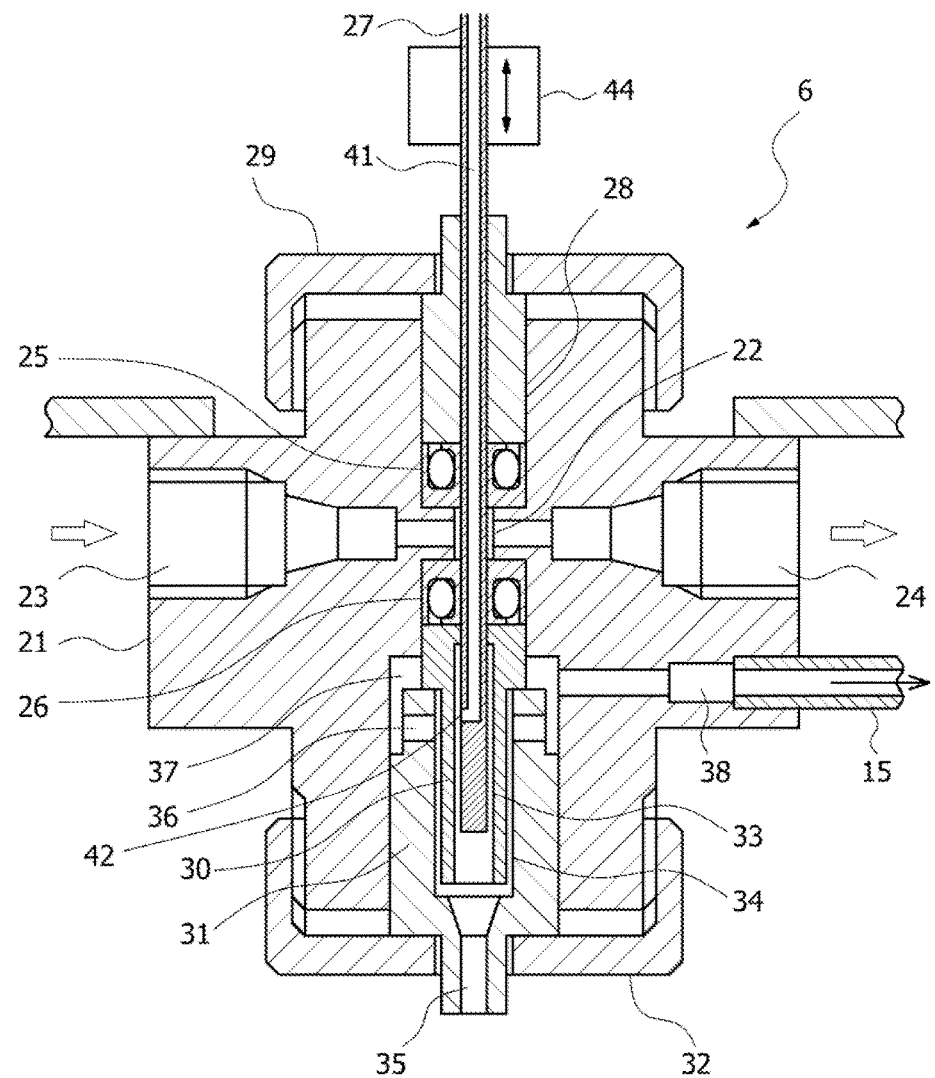
FIG. 2 is a cross section of the sample injection device when a needle is positioned at a washing position.
Figure 2:
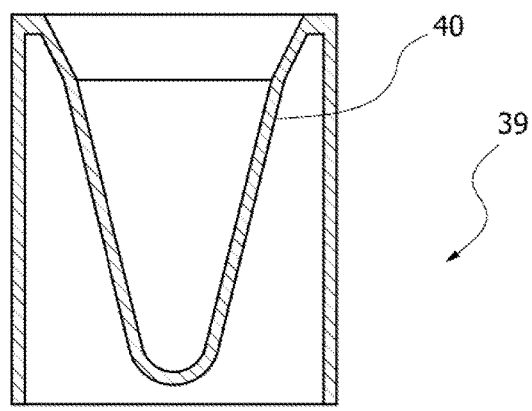
Figure 3:
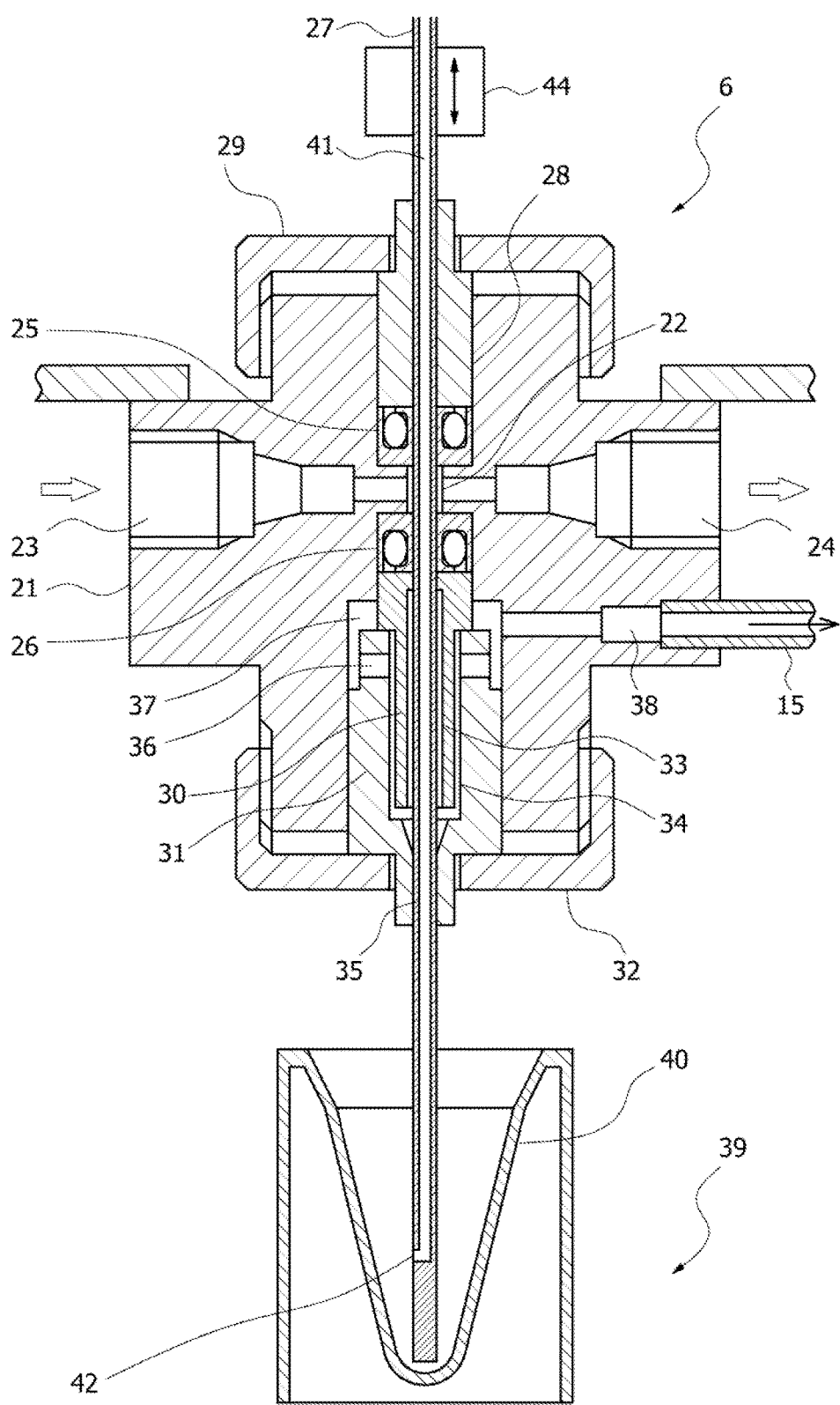
FIG. 3 is a cross section of the sample injection device when the needle is positioned at a sample drawing position.
Figure 4:
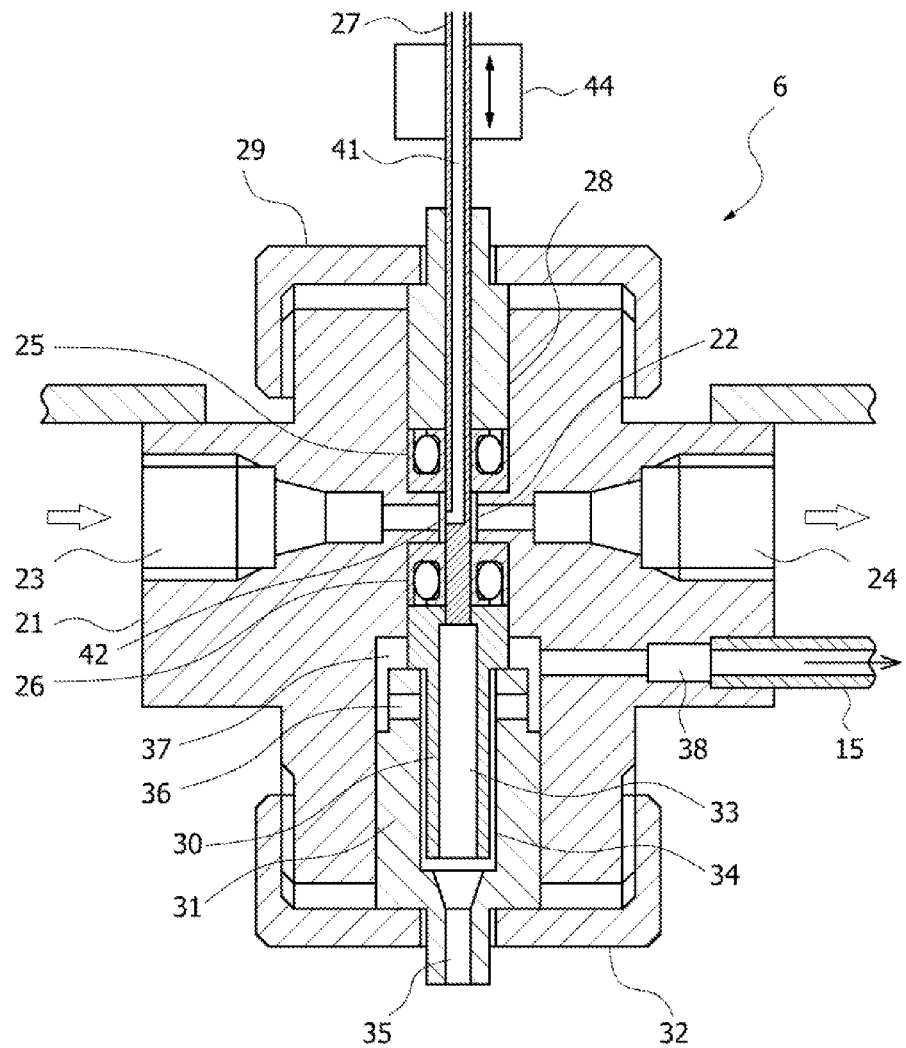
FIG. 4 is a cross section of the sample injection device when the needle is positioned at a sample injection position.
Figure 4:
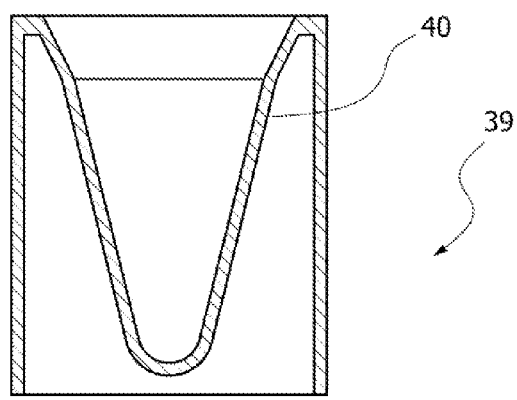

FIGS. 2 to 4 are cross sections of the sample injection device (main body) 6, and FIG. 2 illustrates a state in which the sample injection device 6 is positioned at the washing position, FIG. 3 illustrates a state in which the sample injection device 6 is positioned at the sample drawing position, and FIG. 4 illustrates a state in which the sample injection device 6 is positioned at the sample injection position.

The sample injection device 6 includes the housing 21 as a main component thereof, and in the housing 21, the sample injection portion 22 formed so as to vertically penetrate through the housing 21; an inlet port 23 that extends horizontally from a side wall opening, which is a portion of connection with the channel 5 for the carrier liquid from the 4-way joint 3 (FIG. 1), to open toward the sample injection portion 22; and an outlet port 24 that extends horizontally from a side wall opening, which is a portion of connection with the carrier-liquid channel 7 for the carrier liquid to the column 8 and the detection unit 9 (FIG. 1), to open toward the sample injection portion 22.

The diameter of the sample injection portion 22 on its upper end side thereof is expanded, and a ring-like sealing member 25 is mounted there. The diameter of the sample injection portion 22 on its lower end side is also expanded, and a ring-like sealing member 26 is mounted there.

The ring-like sealing members 25, 26 used in the present embodiment can be constituted by an elastic ring such as a metal ring or a rubber ring arranged inside a groove of a frame member made of polytetrafluoroethylene (PTFE), having a U-shaped section, and formed so as to have an annular shape. However, the present invention is not limited to this, and a general ring-like sealing member with excellent durability, pressure tightness, abrasion resistance, chemical resistance, and the like can be used.

The cylindrical needle 27 is arranged so as to be slidably engaged in a hole formed in the center of the ring-like sealing members 25, 26 so that a part of the needle 27 in the longitudinal direction is disposed inside the sample injection portion 22.

In other words, the cylindrical needle 27 that penetrates through an upper wall and a lower wall of the carrier-liquid channels 5, 7 at the sample injection position (the sample injection portion 22) is provided, and the penetrated portions are sealed with the ring-like sealing members 25, 26.

The sealing member 25 provided on the upper side is nipped between the housing 21 and a guide member 28, and the guide member 28 is fixed with a locking nut 29. The guide member 28 has a guide hole for guiding the needle 27 in the vertical direction.

The sealing member 26 provided on the lower side is nipped between the housing 21 and a cylindrical washing portion forming member 30, and the washing portion forming member 30 is fixed with a locking nut 32 via a guide member 31.

The washing portion forming member 30 is cylindrically shaped and arranged so as to surround the needle 27. With this configuration, the washing portion forming member 30 forms the washing portion 33 for washing the needle 27 on an inner periphery side thereof.

The guide member 31 has an annular space 34 formed so as to surround an outer periphery side of the washing portion forming member 30 including a lower end side thereof, and further includes a guide hole 35 for guiding the needle 27 in the vertical direction, which is in communication with the annular space 34.

The annular space 34 in the guide member 31 is in communication with an annular space 37 inside the housing 21 via a communication hole 36 formed on the guide member 31 in the radial direction.

A discharge port 38 which opens toward an outer wall of the housing 21 is formed starting from the annular space 37 in the housing 21, and the discharge path 15 is connected to the discharge port 38. The discharge path 15 includes the discharge pump 14 (FIG. 1).

Below the housing 21 of the sample injection device 6, more specifically, below the guide hole 35, there is provided a vessel holding portion 39 as a sample drawing portion, and the vessel holding portion 39 holds a sample vessel 40. This vessel 40 also serves as a vessel for dilution (and hemolysis) of the sample. Note that the sample injection device 6 may at least include a configuration in which the sample vessel 40 can be aligned and set; however, the sample injection device 6 may also include a vessel feed mechanism.

The needle 27 is cylindrically shaped and has a hole 41 in an inside thereof. The inner hole 41 is formed from an upper end toward a lower end, and is closed on the lower end side and is opened on an outer peripheral surface as a horizontal hole 42. The height of the horizontal hole from the lower end (the length of the needle 27 in a portion of the needle 27 below the horizontal hole 42) is set so that the portion of the needle 27 below the horizontal hole 42 would not come off from the lower sealing member 26 toward the sample injection portion 22 when the horizontal hole 42 is positioned in the sample injection portion 22, as illustrated in FIG. 4.

Figure 5A:
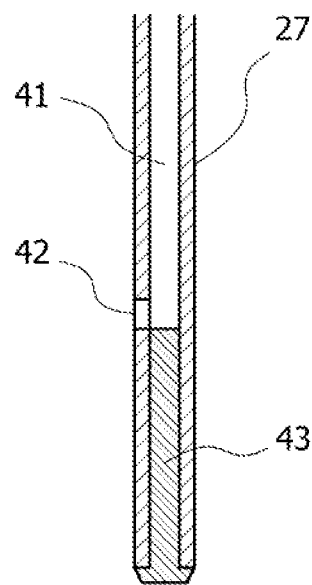
FIG. 5 is a cross section illustrating a method of forming a needle with a horizontal hole structure.
Figure 5B:
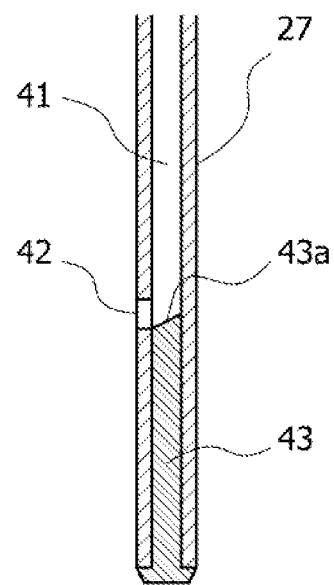

FIG. 5 specifically illustrates a method of forming the needle 27 having the structure of the horizontal hole 42. In FIG. 5(A), after the horizontal hole 42 is formed on the outer peripheral surface of the cylindrical needle 27 a bar-like piece member 43 is inserted through the hole 41 from the side of the lower end of the needle 27, and then the piece member 43 is fixed by bonding or the like to close the lower end side of the needle 27. In addition, in FIG. 5(B), when the piece member 43 is inserted, the piece member 43 is circumferentially aligned with an upper end surface of the piece member 43 as a sloped surface 43a, and thus, the carrier-liquid can be drawn smoothly from the bottom of the hole 41 to the horizontal hole 42, and as a result, congestion and the like of the carrier-liquid can be avoided, and thereby, the drawing of the carrier-liquid is improved.

In addition, the needle 27 is provided with a needle moving unit 44, which can raise and lower the needle 27 to a freely selected vertical position.

The needle moving unit 44 is raised and lowered the needle 27 and is capable of moving the needle 27 to at least a sample drawing position (FIG. 3), at which the horizontal hole 42 is positioned below the sealing member 26 and opens toward the inside of the sample vessel 40, and a sample injection position (FIG. 4), at which the horizontal hole 42 is positioned above the sealing member 26 and open toward the sample injection portion 22 (the carrier-liquid channel).

The needle moving unit 44 is also capable of raising and lowering the needle 27 to move the needle 27 to the washing position (FIG. 2) at which the horizontal hole 42 faces the washing portion 33.

Note that the needle moving unit 44 can be constituted by a progressive step motor or the like, which converts the rotary motion of a rotor (nut) into progressive motion of an nonrotating shaft (screw), for example.

At the position a, the needle 27 is connected with the measurement pump 11 (FIG. 1) on its upper end via the above-described switching valve 16 (FIG. 1). Accordingly, by performing the drawing operation by the measurement pump 11, the sample can be drawn into the inside of the needle 27 through the horizontal hole 42, and by subsequently performing the discharge operation by the measurement pump 11, the sample having been drawn to the inside of the needle 27 can be discharged through the horizontal hole 42.

The measurement pump 11 can also be selectively connected to the upper end of the needle 27 and the dilution-washing liquid tank 53 via the switching valve 16. Specifically, the switching valve 16 connects between the measurement pump 11 and the dilution-washing liquid tank 53 at one position thereof (the position b) and connects between the measurement pump 11 and the needle 27 at the other position (the position a). Accordingly, the measurement pump 11 is capable of discharging the dilution-washing liquid having been drawn from the dilution-washing liquid tank 53 at one position (the position b) of the switching valve 16 to the inside of the needle 27 at the other position (the position a) of the switching valve 16.

Next, a series of operations of the above-described sample injection device 6 will be described with reference to a case of measuring hemoglobin A1c in blood, which is carried out in diabetes testing.

First, a preparation step (a deaeration and carrier-liquid charging step) is performed.

Subsequently, a washing step before sample drawing (51) is performed. In this step, the needle 27 has moved to the washing position at which the horizontal hole 42 faces the washing portion 33 in the washing portion forming member 30 as illustrated in FIG. 2.

S1-1: The switching valve 16 is switched to the position b for connecting the measurement pump 11 and the dilution-washing liquid tank 53, and the measurement pump 11 measures and draws the dilution-washing liquid (washing liquid).

S1-2: After the drawing is completed, the switching valve 16 is switched to the position a for connecting the measurement pump 11 and the needle 27.

S1-3: The discharge pump 14 is turned ON.

S1-4: The measurement pump 11 is caused to discharge, the washing liquid is fed to the needle 27, and then the washing liquid is discharged to the washing portion 33 in the washing portion forming member 30 through the horizontal hole 42 to wash the needle 27 and the washing portion forming member 30.

In this step, because the flow rate of the discharge pump 14 is higher than the flow rate of the measurement pump 11, after the washing is completed, the washing liquid is discharged from the discharge path 15 via the annular space 34, the communication hole 36, the annular space 37, and the discharge port 38 together with the air entered from the guide hole 35. In this step, the washing liquid is mixed with the air to take the form of mist, and thereby, the washing efficiency can be increased, the consumption of the washing liquid can be reduced, and as a result, the needle 27 can be washed in an excellent manner.

S1-5: The discharge pump 14 is turned OFF. In this step, the inner periphery side of the washing portion forming member 30 (the washing portion 33) is filled with the residual washing liquid.

Subsequently, a dilution step (S2) is performed.

S2-1: The switching valve 16 is switched to the position b for connecting the measurement pump 11 and the dilution-washing liquid tank 53, and the dilution-washing liquid (washing liquid) is measured and drawn by using the measurement pump 11.

S2-2: After the drawing is completed, the switching valve 16 is switched to the position a for connecting the measurement pump 11 and the needle 27.

S2-3: The needle moving unit 44 causes the needle 27 to move down to the lowermost position as illustrated in FIG. 3, at which the horizontal hole 42 of the needle 27 faces the inside of the vessel 40 (i.e., at the same position as the sample drawing position).

S2-4: The measurement pump 11 is caused to discharge, the dilution liquid is fed to the needle 27, and allowed to enter the inside of the sample vessel 40 through the horizontal hole 42 of the needle 27.

S2-5: A separately measured sample (blood for testing) transferred manually or automatically into the inside of the vessel 40. Note that the filling of the separately measured sample (blood for testing) into the inside of the vessel 40 is not limited to filling carried out after S2-4, i.e., the filling of the separately measured sample can be previously carried out prior to S2-4.

S2-6: The needle moving unit 44 causes the needle 27 to move upward off the level of the liquid in the inside of the vessel 40 so that the horizontal hole 42 of the needle 27 is positioned at a position at which air can be drawn. Then, the measurement pump 11 is caused to draw the partitioning air to the inside of the needle 27. The partitioning air is used for preventing diffusion of the dilution liquid remaining inside the needle 27 and the dilution sample to be subsequently drawn for stirring at the boundary.

S2-7: The needle moving unit 44 causes the needle 27 to move down again to the lowermost position.

S2-8: The measurement pump 11 is operated to repeatedly carry out drawing and discharge operations to draw and discharge a liquid mixture of the sample and the hemolysis and dilution liquid inside the vessel 40 by using the needle 27, and thereby the liquid mixture inside the vessel 40 is stirred and the sample is uniformly diluted and hemolyzed. Finally, the measurement pump 11 carries out a discharge operation to discharge the partitioning air. This is carried out to prevent the partitioning air from entering the analysis line in the subsequent sample injection step, thereby preventing noise.

Next, a sample drawing and injection step (S3) is performed.

S3-1: The measurement pump 11 is operated to measure and draw the sample at the sample drawing position illustrated in FIG. 3, and thereby, the diluted and hemolyzed sample is drawn from the inside of the vessel 40 to the inside of the needle 27.

S3-2: The needle moving unit 44 causes the needle 27 to move up to the sample injection position as illustrated in FIG. 4, at which the horizontal hole 42 of the needle 27 faces the carrier-liquid channel (the sample injection part 11). Subsequently, the measurement pump 11 is operated for discharge to inject a predetermined amount of sample into the flow of the carrier liquid.

S3-3: The needle moving unit 44 induces the needle 27 to move to the washing position illustrated in FIG. 2. In the course of the movement, contaminants from the sample that adhered to the outside of the needle 27 are squeezed and removed by the sealing member 26 and washed off with the washing liquid filling the washing portion forming member 30.

S3-4: The injected sample is separated into the components of the sample by the column 8 on the downstream side, and the separated components are detected by the detection unit 9.

Next, a washing step is performed after the sample injection (S4).

S4-1: The discharge pump 14 is turned ON.

S4-2: The measurement pump 11 is operated for discharge at the washing position illustrated in FIG. 2 to dispose of the sample remaining in the inside of the needle 27.

S4-3: The switching valve 16 is switched to the position for connecting to the dilution-washing liquid tank 53 and the dilution-washing liquid (washing liquid) is measured and drawn by the measurement pump 11. After the drawing is completed, the switching valve 16 is switched to the position for connecting to the needle 27.

S4-4: The measurement pump 11 is operated for discharge to feed the washing liquid to the needle 27 and wash the inside of the needle 27 and the inside and the outside of the washing portion forming member 30.

S4-5: The discharge pump 14 is turned OFF. In this step, the inner periphery side of the washing portion forming member 30 (the washing portion 33) is filled with the residual washing liquid.

In analyzing the next sample, S2 to S4 are repeated.

The sample injection device according to the present embodiment is configured to include the cylindrical needle 27 which extends in the vertical direction and penetrates through the upper wall and the lower wall of the carrier-liquid channel at the sample injection position (the sample injection portion 22); the ring-like sealing members 25, 26 that seal the penetrated portions; the sample drawing portion 39 arranged below the lower wall and which holds the vessel 40 in which the sample is contained; the needle moving unit 44 capable of causing the needle 27 to move in the vertical direction; and the measurement pump 11 which can be connected with the needle 27 on the upper end thereof, and in the sample injection device, the cylindrical needle 27 includes the inner hole 41 which is closed on the side of the lower end thereof and open on the outer peripheral surface as the horizontal hole 42; the needle moving unit 44 is capable of causing the needle 27 to move in the vertical direction to at least the sample drawing position, at which the horizontal hole 42 is positioned below the lower wall (the sealing member 26) and faces the inside of the vessel 40, and the sample injection position, at which the horizontal hole 42 is positioned above the lower wall (the sealing member 26) and faces the carrier-liquid channel; and the measurement pump 11 which is connected to the cylindrical needle 27 on the upper end thereof and configured to perform the drawing operation when the needle 27 is positioned at the sample drawing position and the discharge operation when the needle 27 is positioned at the sample injection position. Accordingly, the following effects can be obtained.

Specifically, the carrier-liquid channel is not blocked when the sample is injected and the carrier-liquid channel is always in substantially the same state; which enables elimination of the occurrence of sample injection shocks, and thus excellent injection of samples into a constant flow of carrier-liquid can be realized. As a result, an analysis with high precision can be achieved.

In addition, according to the present invention, conventional sample injection valves and the like become unnecessary, and thus, reduction in size and price of the device can be achieved. Furthermore, the present invention has an advantage such that complicated maintenance operations required for conventional sample injection valves are not required.

Further, in particular, by employing the horizontal hole structure for the needle 27 instead of an open tip structure, it becomes unnecessary to cause the needle 27 to go from the lower wall toward the sample injection portion 22 when injecting a sample, and thus the needle 27 can always remain being penetrated through the lower wall. Accordingly, the general ring-like sealing members 25, 26 can be applied for the penetrated portions. With this configuration, durability and reliability can be improved.

In addition, in the present embodiment, the washing position is set at a position between the sample drawing position and the sample injection position outside the carrier-liquid channel as the position for the needle 27 to move by being induced by the needle moving unit 44, and the present embodiment is configured to further include the washing liquid feed device (the measurement pump 11 and the like) capable of feeding the washing liquid to the inside of the needle 27, to discharge the washing liquid through the horizontal hole 42, when the needle 27 is at the washing position; and the washing liquid recovery device (the discharge pump 14 and the like) which recovers the washing liquid flowing out through the horizontal hole 42 when the needle 27 is positioned at the washing position by surrounding the needle 27. Thereby the inside and the outside of the needle 27 can be securely washed before and after the sample drawing and injection step. Furthermore, with the needle washing mechanism formed integrally with the mechanism of the sample injection device, the mechanism may not require an additional area for installation of a separately provided washing unit.

In addition, in the present embodiment, the washing liquid feeding device includes the measurement pump 11, and the measurement pump 11 can be connected selectively with the needle 27 on the upper end thereof and the washing liquid tank 53 via the switching valve 16 and can discharge and feed the washing liquid drawn from the washing liquid tank 53 at one position (the position b) of the switching valve 16 to the needle 27 at the other position (the position a) of the switching valve 16. Thereby the washing liquid feed device enables easy feeding of the washing liquid, and as a result, the washing liquid feeding device is highly useful.

In addition, in the present embodiment, the washing liquid recovery device includes the cylindrical washing portion forming member 30, which surrounds the needle 27 to form the washing portion 33; and the discharge pump 14, which is connected to the space 34 surrounding the washing portion forming member 30 on the lower end thereof, and capable of performing the drawing operation. With this configuration, the washing of the needle 27 and the recovery of the washing liquid after the washing is completed can be securely performed.

In addition, in the present embodiment, the washing liquid also serves as a dilution liquid for the sample, and the washing liquid feeding device is capable of feeding the washing liquid that also serves as the dilution liquid to the inside of the needle 27, to discharge the washing liquid through the horizontal hole 42 to the inside of the vessel 40, when the needle 27 is at the sample drawing position. Thereby, the dilution step can be readily implemented, and as a result, the present embodiment is highly useful.

In addition, the flow-type analysis device according to the present embodiment includes the above-described sample injection device 6; and the detection device (the detection unit 9) arranged in the carrier-liquid channel on the downstream side of the sample injection device 6 and configured to detect components of the sample. Thereby, the analysis device enables elimination of the occurrence of sample injection shocks, and adverse effects on the analysis can be prevented. As a result, analysis with high precision and a high performance can be achieved.

In addition, the measurement method for hemoglobin components according to the present embodiment uses the above-described sample injection device 6 to inject blood as the sample into the carrier-liquid channel, and separates and detects the hemoglobin components contained in the blood and measures the amount of the components (hemoglobin A1c and the like). Thereby, the method is capable of contributing to improving the precision and the speed of diabetes testing. Note that a publicly known method can be used as a method for separating and detecting hemoglobin contents contained in blood and measuring the amount of the contents, and separation analysis by a general liquid chromatography method employing the system including a sample injection part, a sample separation part including a separation column, and a detection part is well known to one skilled in the art. However, the scope of application of the device according to the present invention is not limited to this.

Note that the embodiment illustrated in the Figures is a mere example of the present invention, and the present invention of course includes not only the invention directly disclosed by the above-described embodiment but also various improvements and modifications that may be made by one skilled in the art within the scope of the present invention as claimed in the claims.

INDUSTRIAL APPLICABILITY

The sample injection device for a flow-type analysis device, the flow-type analysis device which uses the sample injection device, and the measurement method for hemoglobin components according to the present invention can be preferably used in various types of analyses and have high levels of industrial applicability.

REFERENCE SYMBOL LIST

1 First liquid feed pump
2 Second liquid feed pump
3 4-way joint
4 Discharge path
5 Carrier-liquid channel
6 Sample injection device (main body)
7 Carrier-liquid channel
8 Column
9 Detection unit
10 Discharge path
11 Measurement pump
12 Pipe
13 Pipe
14 Discharge pump
15 Discharge path
16 Switching valve
17 Drain valve
18 Pressure sensor
21 Housing
22 Sample injection portion
23 Inlet port
24 Outlet port
25, 26 Sealing member
27 Needle
28 Guide member
29 Locking nut
30 Washing portion forming member
31 Guide member
32 Locking nut
33 Washing portion
34 Annular space
35 Guide hole
36 Communication hole
37 Annular space
38 Discharge port
39 Vessel holding portion (sample drawing portion)
40 Vessel
41 Hole
42 Horizontal hole
43 Piece member
44 Needle moving unit
50 Reagent kit
51 First carrier-liquid tank
52 Second carrier-liquid tank
53 Dilution-washing liquid tank
54 Deaeration device

The invention claimed is:

1. A sample injection system for flow-type analysis configured to inject a sample into a carrier-liquid channel, the system comprising:
a cylindrical needle which extends in a vertical direction and penetrates through portions of an upper wall and a lower wall of the carrier-liquid channel at a sample injection position;
ring-like sealing members that seal the penetrated portions of the upper and lower walls;
a vessel frame with an interior surface defining a volume therein, the vessel frame positioned below the lower wall;
a needle moving unit capable of causing the cylindrical needle to move in the vertical direction;
a measurement pump which is operatively connected with the cylindrical needle on an upper end of the cylindrical needle; and
a washing portion of a main body below the carrier-liquid channel,
wherein the cylindrical needle includes an inner hole therein and a horizontal hole between an outer surface of the cylindrical needle and the inner hole, the cylindrical needle closed below the horizontal hole,
wherein the needle moving unit is capable of causing the cylindrical needle to move in the vertical direction to at least a sample drawing position at which the horizontal hole is positioned below the lower wall and faces the interior surface of the vessel frame and a sample injection position at which the horizontal hole is positioned above the lower wall and faces the carrier-liquid channel, wherein the washing portion of the main body is configured so that the cylindrical needle is positionable at a washing position set between the sample drawing position and the sample injection position such that the horizontal hole is positioned below the lower wall and above the vessel frame, wherein the measurement pump is operatively connected to the cylindrical needle on the upper end of the cylindrical needle and is configured to perform a drawing operation when the cylindrical needle is positioned at the sample drawing position and a discharge operation when the cylindrical needle is positioned at the sample injection position, and wherein the measurement pump is operatively connected to a washing liquid tank via a switching valve configured to draw the washing liquid from the washing liquid tank to the measurement pump at one position of the switching valve and to discharge the washing liquid to the cylindrical needle at another position of the switching valve.

2. The sample injection system for flow-type analysis according to claim 1, wherein the washing portion is defined by a cylindrical washing portion forming member which surrounds the cylindrical needle.

3. The sample injection system for flow-type analysis according to claim 2, further comprising a discharge pump which is connected to a space surrounding the washing portion forming member and is configured to perform a drawing operation.

4. A flow-type analysis system comprising:
the sample injection system according to claim 1; and
a detection device which is arranged in the carrier-liquid channel on a downstream side of the sample injection system and configured to detect components of the sample.

5. A measurement method for hemoglobin components which uses the sample injection system according to claim 1, the method comprising:
injecting blood as the sample into the carrier-liquid channel; and
separating and detecting hemoglobin components contained in the blood and measuring an amount of the components.

6. The measurement method for hemoglobin components according to claim 5, the method comprising a stirring step of homogeneously diluting and hemolyzing the sample by causing the measurement pump to repeat the drawing and discharging operations, by drawing and returning the mixture of the sample in the vessel and the dilution liquid with the needle connected with the measurement pump, and thereby stirring the mixture in the vessel.

7. A stirring method for homogeneously diluting the sample by causing the measurement pump to repeat drawing and discharging operations and by drawing and returning a mixture of the sample in the vessel and the dilution liquid with the needle connected with the measurement pump by using the sample injection system according to claim 1.

8. A sample injection system for flow-type analysis configured to inject a sample into a carrier-liquid channel, the system comprising:

a cylindrical needle which extends in a vertical direction and penetrates through portions of an upper wall and a lower wall of the carrier-liquid channel at a sample injection position;
ring-like sealing members that seal the penetrated portions of the upper and lower walls;
a vessel frame with an interior surface defining a volume therein, the vessel frame positioned below the lower wall;
a needle moving unit capable of causing the cylindrical needle to move in the vertical direction;
a measurement pump which is operatively connected with the cylindrical needle on an upper end of the cylindrical needle; and
a washing portion of a main body below the carrier-liquid channel,
wherein the cylindrical needle includes an inner hole therein and a horizontal hole between an outer surface of the cylindrical needle and the inner hole, the cylindrical needle closed below the horizontal hole,
wherein the needle moving unit is capable of causing the cylindrical needle to move in the vertical direction to at least a sample drawing position at which the horizontal hole is positioned below the lower wall and faces the interior surface of the vessel frame and a sample injection position at which the horizontal hole is positioned above the lower wall and faces the carrier-liquid channel,
wherein the washing portion of the main body is configured so that the cylindrical needle is positionable at a washing position set between the sample drawing position and the sample injection position such that the horizontal hole is positioned below the lower wall and above the vessel frame,
wherein the measurement pump is operatively connected to the cylindrical needle on the upper end of the cylindrical needle and is configured to perform a drawing operation when the cylindrical needle is positioned at the sample drawing position and a discharge operation when the cylindrical needle is positioned at the sample injection position, and
wherein the measurement pump is configured to feed a washing liquid which also serves as the dilution liquid for a sample to the inner hole of the cylindrical needle to discharge the dilution liquid through the horizontal hole to the volume in the vessel frame when the cylindrical needle is positioned at the sample drawing position.

9. A sample injection system for flow-type analysis configured to inject a sample into a carrier-liquid channel, the system comprising:
a cylindrical needle which extends in a vertical direction and penetrates through portions of an upper wall and a lower wall of the carrier-liquid channel at a sample injection position;
ring-like sealing members that seal the penetrated portions of the upper and lower walls;
a vessel frame with an interior surface defining a volume therein, the vessel frame positioned below the lower wall;
a needle moving unit capable of causing the cylindrical needle to move in the vertical direction;
a measurement pump which is operatively connected with the cylindrical needle on an upper end of the cylindrical needle; and
a washing portion of a main body below the carrier-liquid channel, wherein the cylindrical needle includes an inner hole therein and a horizontal hole between an outer surface of the cylindrical needle and the inner hole, the cylindrical needle closed below the horizontal hole, wherein the needle moving unit is capable of causing the cylindrical needle to move in the vertical direction to at least a sample drawing position at which the horizontal hole is positioned below the lower wall and faces the interior surface of the vessel frame and a sample injection position at which the horizontal hole is positioned above the lower wall and faces the carrier-liquid channel, wherein the washing portion of the main body is configured so that the cylindrical needle is positionable at a washing position set between the sample drawing position and the sample injection position such that the horizontal hole is positioned below the lower wall and above the vessel frame, wherein the measurement pump is operatively connected to the cylindrical needle on the upper end of the cylindrical needle and is configured to perform a drawing operation when the cylindrical needle is positioned at the sample drawing position and a discharge operation when the cylindrical needle is positioned at the sample injection position, and wherein the measurement pump is configured to feed a washing liquid to the inner hole of the cylindrical needle and discharge the washing liquid from the inner hole through the horizontal hole when the cylindrical needle is positioned at the washing position.

10. The sample injection system for flow-type analysis according to claim 9, further comprising a discharge pump configured to recover the washing liquid that flows from the inner hole through the horizontal hole when the cylindrical needle is positioned at the washing position by channeling the washing liquid to the discharge pump through a washing portion forming member surrounding the cylindrical needle.

* * * * *